United States Patent [19]

Neville, Jr. et al.

[11] Patent Number: 5,167,956
[45] Date of Patent: Dec. 1, 1992

[54] IMMUNOTOXIN WITH IN-VIVO T CELL SUPPRESSANT ACTIVITY

[75] Inventors: David M. Neville, Jr., Bethesda; Joshua E. Scharff, Rockville, both of Md.

[73] Assignee: The United States of America as represented by the Department of Health and Human Services, Washington, D.C.

[21] Appl. No.: 653,164

[22] Filed: Feb. 11, 1991

[51] Int. Cl.$^5$ ...................... A61K 39/44; C07K 15/28
[52] U.S. Cl. ............................ 424/85.91; 530/391.7; 530/391.9
[58] Field of Search ............... 424/85.91; 530/389, 530/391, 391.7, 391.9

[56] References Cited

FOREIGN PATENT DOCUMENTS 0306943 3/1989 European Pat. Off. .

OTHER PUBLICATIONS

Pastan et al (1991) Science 254:1173–1177.
Hauser (1991) Science 254:1167–1172.
Greenfield et al (1987) Science 238:536–539.
Johnson et al (1988) J. Biol. Chem. 263(3):1295–1300.
Myers et al (1989) J. Immunol. Methods 121:129–142.
Neville, Jr. et al. (1989) J. Biol. Chem. 264(25):14653–61.
Urban et al (1988) Cell 54:577–592.

Primary Examiner—Christine M. Nucker
Assistant Examiner—Kay Kim
Attorney, Agent, or Firm—Needle & Rosenberg

[57] ABSTRACT

The present invention relates to an immunotoxin. The invention further relates to a method of treating T cell leukemias and lymphomas, graft-versus-host diseases, and autoimmune diseases by administering an immunotoxin.

3 Claims, 1 Drawing Sheet

IMMUNOTOXIN WITH IN-VIVO T CELL SUPPRESSANT ACTIVITY

BACKGROUND OF THE INVENTION

1. Field of the Invention

The present invention relates to an immunotoxin. The invention further relates to a method of treating T cell leukemias or lymphomas, graft-versus-host diseases, and autoimmune diseases by administering an immunotoxin.

2. Background Information

Immunotoxins are toxins with altered receptor specificities. The alteration is achieved by coupling a monoclonal antibody (mAb) or growth factor to the toxin or toxin fragment. Plant and bacterial protein toxins intoxicate cells by a multi-step process whereby different toxin domains sequentially interact with cellular components. The intoxication pathway at a minimum consists of surface receptor binding, toxin processing, intracellular routing of toxin A chains to the cytosol, and enzymatic inactivation of protein synthesis (Neville and Hudson (1986) Ann. Rev. Biochem. 55:195). The goal of immunotoxin research has been to achieve targeted cell killing comparable to the enormous but indiscriminate cell killing power of the native toxins. An equally important goal has been to maintain the low non-target cell toxicity of toxin A chains, which lack cell receptor binding and membrane translocation functions (Youle and Neville (1982) J. Biol. Chem. 257:1598; Neville (1986) in CRC Crit. Rev. Therap. Drug Carrier Syst., CRC Press Inc., 2:329; Immunotoxins, Frankel ed.(1988) Kluwer Academic Publishers). Because of this latter consideration most in vivo clinical studies have focused on A chain immunotoxins or immunotoxins with truncated B chains lacking the receptor binding domain. While some clinical results have been encouraging, the reproducible achievement of both goals is at present uncertain (Program and Abstracts 2nd Int. Symposium on Immunotoxins, June 1990, Lake Buena Vista, Fla.).

Recently, Youle and co-workers have introduced highly efficacious holo-immunotoxins based on diphtheria toxin (DT) binding mutants (Greenfield et al. (1987) Science 238:536; Johnson et al. (1988) J. Biol. Chem. 263:1295; Johnson et al (1989) J. Neurosurg. 70:240). These DT binding site mutants were equal to the wild-type immunotoxins in potency when directed at the human transferrin receptor (TFR) or human CD3, a component of the T cell receptor complex. Since the binding of the mutants was only 1/100–1/1000 of native DT, the toxin receptor appeared to be not needed along the intoxication pathway. This conclusion is limited to CD3 and TFR directed immunotoxins because similar immunotoxins directed at CD5 and the high-molecular weight-melanoma-associated antigen are relatively nontoxic (Neville et al. (1989) J. Biol. Chem. 264:14653). On the basis of data obtained with acid-cleavable conjugates which released free DT or the DT binding site mutant CRM9 in acidified endosomes, it was concluded that the DT receptor participates in the optimal intracellular routing of DT and many DT conjugates (Neville et al. (1989) J. Biol. Chem. 264:14653). It was also concluded that CD3 and TFR can perform the same routing function as the DT receptor, thus obviating the requirement of a DT receptor interaction for the binding site mutant conjugates anti-CD3-CRM9 and TF-CRM9 (Intracellular routing of ricin based immunotoxins via the ricin receptor leading to enhanced efficacy has also been reported. Youle et al. (1981) Cell 23:551; Marsh and Neville (1986) Biochem. 25:4461; Youle and Colombatti (1987) J. Biol. Chem. 262:4676). Since anti-CD3-CRM9 appears to achieve optimal routing with low non-target cell toxicity as judged by in vitro assays, the present invention relates to a method of eradicating human CD3 bearing tumors in vivo.

The present invention provides in one embodiment, the immunotoxin anti-CD3-CRM9. The invention provides, in further embodiments, methods of treating T cell leukemias or lymphomas, graft-versus-host diseases, and autoimmune diseases by administering the immunotoxin anti-CD3-CRM9.

SUMMARY OF THE INVENTION

It is a general object of this invention to provide an immunotoxin.

It is a specific object of this invention to provide an immunotoxin corresponding to anti-CD3-CRM9 or derivatives thereof.

It is a further object of the invention to provide a method of treating T cell leukemias or lymphomas which carry the CD3 epitope.

It is a another object of the invention to provide a method of treating graft-versus-host disease.

It is a further object of the invention to provide a method of treating autoimmune diseases.

Further objects and advantages of the present invention will be clear from the description that follows.

In one embodiment, the present invention relates to an immunotoxin comprising anti-CD3-CRM9 or derivatives thereof.

In another embodiment, the present invention relates to a pharmaceutical composition comprising anti-CD3-CRM9 or derivatives thereof in an amount effective to treat T cell leukemias or lymphomas which carry the CD3 epitope, graft-versus-host disease or autoimmune diseases, and a pharmaceutically acceptable diluent, carrier, or excipient.

In a further embodiment, the present invention relates to a method of treating T cell leukemias or lymphomas which carry the CD3 epitope in an animal comprising administering to an animal anti-CD3-CRM9 or derivatives thereof under conditions such that the leukemias or lymphomas regress.

In another embodiment, the present invention relates to a method of treating graft-versus-host disease in an animal comprising administering to an animal anti-CD3-CRM9 or derivatives thereof under conditions such that the symptoms of the graft-versus-host disease improve.

In a further embodiment, the present invention relates to a method of treating autoimmune diseases in an animal comprising administering to the animal anti-CD3-CRM9 or derivatives thereof under conditions such that the symptoms of the autoimmune disease improve. In one preferred embodiment, the autoimmune disease is AIDS.

DETAILED DESCRIPTION OF THE INVENTION

Figure 1:
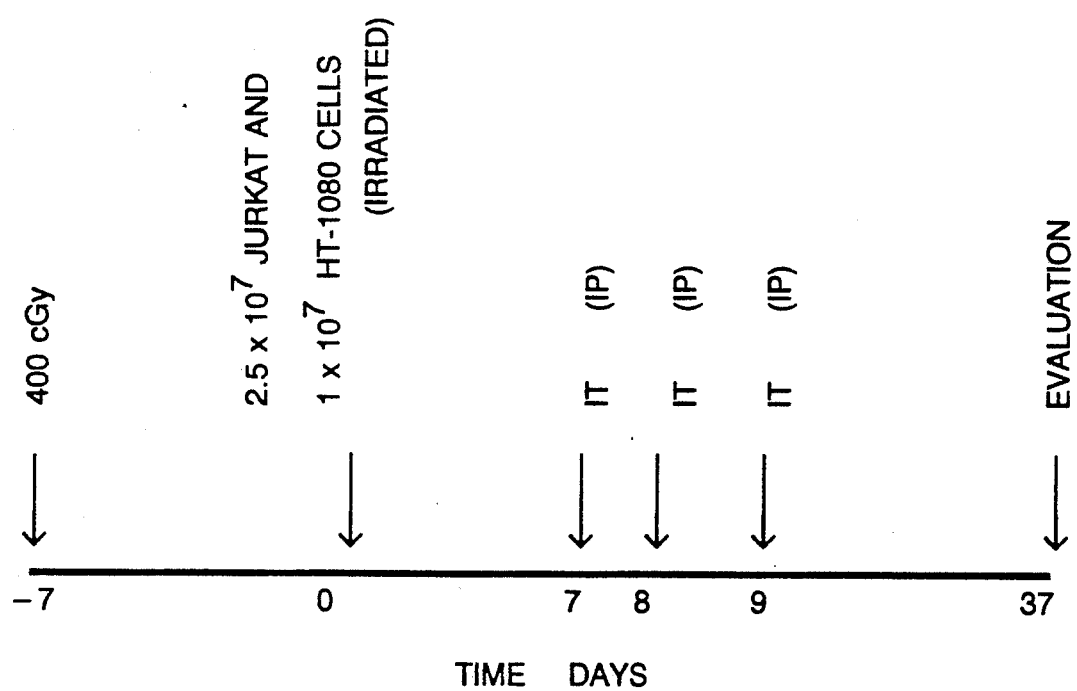
FIG. 1. Nude mice bg/nu/xid maintained in a semi-sterile environment are preconditioned with 400 cGy whole body $^{137}$Cs $\gamma$ radiation on day $-7$. On day 0, $2.5 \times 10^7$ Jurkat cells (human T cell leukemia CD3+, CD4+, CD5+) are injected subcutaneously with $1 \times 10^7$ HT-1080 feeder cells (human sarcoma) which have received 6000 cGy. Jurkat cells were passaged every other week in mice as subcutaneous tumors and dissociated by collagenase/dispase prior to inoculation. This cell population exhibits a 40% inhibition of protein synthesis after 5 hours exposure to $10^{-11}$M anti-CD3-DT. Clones isolated from this population by infinite dilution exhibit varying sensitivity to anti-CD3-DT (4 less sensitive, 3 more sensitive) corresponding to a 1.5 log variation in dose response curves. Immunotoxin treatment is given by intraperitoneal injection starting on day 7 when the tumor is visibly established. Evaluation takes place on day 37.

The present invention relates to an immunotoxin.

In one embodiment, the present invention relates to an immunotoxin comprising anti-CD3-CRM9 or derivatives thereof. The design of successful derivatives of anti-CD3-CRM9 depend upon understanding how the unique concentration of anti-CD3-CRM9 achieves its biological effect. The toxin moiety CRM9 retains its toxic function, and membrane translocation function to the cytosol in full amounts. The loss in binding function located in the C terminus of the protein diminishes systemic toxicity by reducing binding to non-target cells. The routing function normally supplied by the toxin binding function is supplied by the targeting antibody anti-CD3. The essential routing pathway is (1) localization to coated pits for endocytosis, (2) escape from lysosomal routing, and (3) return to the plasma membrane. Any antibody which can route in this manner will be effective with CRM9, irrespective of which epitope the antibody is directed. Thus, a wide variety of cell types can in principle be targeted. When antibodies dissociate from their receptors due to changes in receptor configuration induced in certain receptors as a consequence of endosomal acidification, they enter the lysosomal pathway. This can be prevented or minimized by directing the antibody towards an ectodomain epitope on the same receptor which is closer to the plasma membranes (Ruud, et al (1989) Scand. J. Immunol. 29:299; Herz et al (1990) J. Biol. Chem. 265:21355). Other DT binding site mutants can be used to form derivatives by changing amino acids in the C terminus which can reduce the binding function as long as the translocation function is maintained.

An example of a series of derivatives which is likely to be effective are antibody-CRM9 conjugates directed at unique V$\alpha$ and V$\beta$ gene segment products of the T cell receptor. Some of these epitopes appear to be biased towards specific autoimmune processes. Such conjugates should be useful in specific autoimmune diseases (Kappler et al (1987) Cell 49:263; Urban et al (1988) Cell 54:577).

Both acid-cleavable and non-cleavable protein cross-linking reagents can be used in the construction of antibody-diphteria toxin binding-site mutant conjugates like anti-CD3-CRM9 (Neville et al. (1989) J. of Biol. Chem. 264:14653-14661); preferred are non-cleavable cross-linkers, such as bismaleimidohexane and m-maleimidobenzoyl-N-hydroxysuccinimide ester. The synthesis of acid-cleavable protein cross-linking reagents based on orthoester, acetal, and ketal functionalities has been described (Srinivasachar and Neville (1989) Biochemistry 28:2501-2509). The unique feature of these functionalities is that their observed hydrolytic rate constants increase 10-fold for each drop in pH, a consequence of specific $H_3O^+$ catalysis leading to a carbonium ion intermediate (Cordes and Bull (1974) Chem. Rev. 74:581-603). Moreover, these functionalities are resistant to base catalysis permitting manipulation and storage at alkaline pH. The cross-linking reagents react with proteins via heterobifunctional groups (maleimide and N-hydroxysuccinimide ester) of homobifunctional groups (bis-maleimide). The maleimide cross-linking is accomplished by prior protein thiolation with iminothiolane. Cross-linked proteins exhibit first-order dissociation under acid conditions. The $t_{\frac{1}{2}}$ at pH 5.5 varies between 0.1 and 130 h for a series of six different cleavable cross-linkers (Srinivasachar and Neville (1989) Biochemistry 28:2501-2509).

In another embodiment, the present invention relates to a pharmaceutical composition comprising anti-CD3-CRM9 or derivatives thereof in an amount effective to treat T cell leukemias or lymphomas which carry the CD3 epitope, graft-versus-host disease or autoimmune diseases, and a pharmaceutically acceptable diluent, carrier, or excipient. One skilled in the art will appreciate that the amounts to be administered for any particular treatment protocol can readily be determined. Suitable amounts might be expected to fall within the range of 7.5 to 75 $\mu$g per kg of body weight.

In a further embodiment, the present invention relates to a method of treating T cell leukemias or lymphomas which carry the CD3 epitope in an animal comprising administering to an animal anti-CD3-CRM9 or derivatives thereof under conditions such that the leukemias or lymphomas regress. Appropriate concentrations and dosage unit sizes can be readily determined by one skilled in the art.

In another embodiment, the invention relates to a method of treating an immune system disorder not involving T cell proliferation which is amenable to T cell suppression. In a specific embodiment, the present invention relates to a method of treating graft-versus-host disease (GVHD) in an animal comprising administering to an animal anti-CD3-CRM9 or derivatives thereof under conditions such that the symptoms of the graft-versus-host disease improve. GVHD is a morbid complication of bone marrow transplantation which is often performed as anti-leukemia/lymphoma therapy. GVHD is caused by circulating donor T cells within the host which are acquired in bone marrow grafts unless specifically depleted prior to grafting (Gale and Butturini (1988) Bone Marrow Transplant 3:185; Devergie et al.(1990) ibid 5:379; Filipovich et al. (1987) Transplantation 44). Successful donor T cell depletion techniques have been associated with a higher frequency of graft rejection and leukemia relapses (Gale and Butturini (1988) Bone Marrow Transplant 3:185; Devergie et al.(1990) ibid 5:379; Filipovich et al. (1987) Transplantation 44). Therefore, the donor T cells appear to aid engraftment and to provide a graft-versus-leukemia effect as well as causing GVHD. Because the T cell burden following bone marrow transplantation is low for the first 14 days (<10% of normal) the log kill of donor T cells would be proportionally enhanced (Marsh and Neville (1987) Ann. N.Y. Acad. Sci. 507:165; Yan et al., submitted; Gale and Butturini (1988) Bone Marrow Transplant 3:185; Devergie et al.(1990) ibid 5:379; Filipovich et al. (1987) Transplantation 44). It is expected that donor T cells can be eliminated at set times during the early post transplantation period using the present method. In this way the useful attributes of grafted T cells might be maximized and the harmful effects minimized.

In a further embodiment, the present invention relates to a method of treating autoimmune diseases in an animal comprising administering to the animal anti-CD3-CRM9 or derivatives thereof under conditions such that the symptoms of the autoimmune disease improve. In one preferred embodiment, the autoimmune disease is AIDS. Radiation induced T cell ablation with concomitant high dose zidovudine therapy followed by bone marrow transplantation has been reported to eradicate HIV-1 infection in one case (Holland et al. (1989) Ann. Int. Med. 111:973). Cyclophosphamide, a T cell suppressive reagent, has been shown to be beneficial in treating murine AIDS (Simard and Joliceur (1991) Science 251:305). Anti-CD3-CRM9 can provide extensive T cell ablation without the requirement of bone marrow reconstitution.

Anti-T cell hemi-immunotoxins (mAbs conjugated to ricin A chain) have been used clinically as T cell suppressants for the treatment of GVHD, rheumatoid arthritis and T cell leukemia (Program and Abstracts 2nd Int. Symposium on Immunotoxins, June 1990, Lake Buena Vista, Fla.; Byers et al. (1990) Blood 75:1426). Some positive effects have been noted. The immunotoxin described here is more toxic on a weight basis than hemi-immunotoxins, but at tolerated doses exhibits an apparent 3 log kill of targeted cells at target cell burdens encountered clinically. This constitutes a favorable therapeutic margin. Most human sera contain anti-DT neutralizing antibodies from childhood immunization (Johnson et al. (1989) J. Neurosurg. 70:240). To compensate for this the therapeutic dose of anti-CD3-CRM9 can be appropriately raised without affecting the therapeutic margin. Alternatively, CRM197 a non-toxic DT mutant reactive with neutralizing antisera, could be administered prior to the conjugate.

The present invention will be illustrated in further detail in the following non-limiting examples.

EXAMPLE 1

Establishment of Tumors

The experimental design of the studies that give rise to the present invention was dictated by the goal of having an animal model as closely relevant to human in vivo tumor therapy as possible. In order to minimize the host killer cell immune response, bg/nu/xid strain of nude mice were used (Kamel-Reid and Dick (1988) Science 242:1706). The human T cell leukemia cell line, Jurkat, was chosen because of previous studies with this line and its relatively normal average complement of CD3 receptors (Preijers et al. (1988) Scand. J. Immunol. 27:553). The line was not cloned so that receptor variation among individual cells existed (FIG. 1 legend). A scheme was developed whereby well established tumors of constant mass equal to 0.1% of body weight ($\sim 4 \times 10^7$ cells) could be achieved 7 days after inoculation of Jurkat cells (see FIG. 1 and Dillman et al. (1988) Cancer Res. 15:5632). This required prior irradiation and inoculation with lethally irradiated helper feeder cells (see FIG. 1 and Dillman et al. (1988) Cancer Res. 5:5632).

EXAMPLE 2

Guinea Pig Studies

Immunotoxin toxicity studies were performed in guinea pigs, an animal (like humans) with a high sensitivity to diphtheria toxin (mice are highly resistant to diphtheria toxin). Therapy of CRM9 conjugates was set at ⅓ the guinea pig minimum lethal dose. In this study, minimum lethal dose (MLD) is defined as the minimum tested dose which results in both non-survivors and survivors over a 4 week evaluation period. All animals survive when a MLD is reduced by 0.5. MLD was evaluated in guinea pigs 300–1000 g by subcutaneous injection. The following MLDs were found listed as $\mu g$ of toxin/kg body weight; DT, 0.15; CRM9, 30; anti-CD5-DT (cleavable), 0.65; anti-CD5-CRM9 (non-cleavable), 150. Finally, the therapeutic efficacy of the immunotoxin treatment in producing tumor regressions was compared to graded doses of whole body irradiation which resulted in similar tumor regressions.

EXAMPLE 3

Comparison of Immunotoxins

Several types of immunotoxins were compared in this study. They were synthesized as previously described by thiolating both the monoclonal antibody moiety and the toxin moiety and then crosslinking the bismaleimide crosslinkers (Neville et al. (1989) J. Biol. Chem. 264:14653). Purification was performed by size exclusion HPLC columns and fractions containing 1:1 toxin::antibody mol ratios were isolated for these studies. Conjugates made with an acid-labile crosslinker bis-maleimidoethoxy propane were compared with a non-cleavable, bis-maleimidohexane. Conjugates made with this cleavable crosslinker have been shown to hydrolyze within the acidifying endosome releasing free toxin moieties with half-times of hydrolysis measured at pH 5.5 of 36 mins (Neville et al. (1989) J. Biol. Chem. 264:14653).

The results of this study are tabulated in Table I. Non-treatment groups such as group 10, groups treated with anti-CD5 immunotoxins (groups 5 and 6), and group 4 treated with a mixture of anti-CD3 and CRM9 did not show regression. The vascularized tumor nodules that weighed 20 mg on day 7 grew to between 1.5 to 7.8 g on day 37 and weighed between 7.9 and 11.6 on day 56. No late spontaneous regressions were noted. In contrast, group 1 consisting of treatment with anti-CD3-CRM non-cleavable conjugate (NC) given at 25 $\mu g/kg$ on days 7, 8, and 9 (see FIG. 1 time line) showed only 1 tumor out of 6 by day 37. Some of the remaining animals were subject to autopsy and they failed to reveal residual tumor or even scaring. Tumors identified as regressed on day 37 by superficial inspection did not reappear during the course of the study (56 days).

TABLE 1

| IMMUNOTOXIN AND RADIATION TREATMENT ON SUBCUTANEOUS HUMAN T CELL TUMORS (JURKAT) IN NUDE MICE | | | |
| --- | --- | --- | --- |
| GROUP TREATMENT | DOSE (intraperitoneal) | ANIMALS BEARING TUMORS AT DAY 37/GROUP ANIMALS | % TUMORS REGRESSIONS |
| 1    Anti-CD3—CRM9 (NC)[a] | 25 $\mu g/kg$. × 3d | 1/6 | 83 |
| 2    Anti-CD3—CRM9 (NC) | 19 $\mu g/kg$. × 2d | 1/4 | 75 |
|       Anti-CD5—CRM9 (C) | 19 $\mu g/kg$. × 2d | | |
| 3    Anti-CD3—CRM9 (C) | 25 $\mu g/kg$. × 3d | 2/4 | 50 |
| 4    Anti-CD3+CRM9 | 25 $\mu g/kg$. × 3d | 4/4 | 0 |

TABLE 1-continued

IMMUNOTOXIN AND RADIATION TREATMENT ON SUBCUTANEOUS HUMAN T CELL TUMORS (JURKAT) IN NUDE MICE

| GROUP | TREATMENT | DOSE (intraperitoneal) | ANIMALS BEARING TUMORS AT DAY 37/GROUP ANIMALS | % TUMORS REGRESSIONS |
|---|---|---|---|---|
| 5 | Anti-CD5—CRM9 (C) | 25 μg/kg. × 3d | 5/5 | 0 |
| 6 | Anti-CD5—DT (NC) | 25 μg/kg. × 1d | 9/9 | 0 |
| 7 | γradiation $^{137}$Cs | 400 cGy | 2/2 | 0 |
| 8 | γradiation $^{137}$Cs | 500 cGy | 3/6 | 50 |
| 9 | γradiation $^{137}$Cs | 600 cGy | 0/2[b] | 100 |
| 10 | None | | 6/6 | 0 |

[a]Anti-CD3 refers to the monoclonal antibody UCHT1 and was purchased from Oxoid USA, Inc. Anti-CD5 refers to the monoclonal antibody T101 and was a gift from Hybritech (San Diego). NC and C refer, respectively, to non-cleavable and cleavable conjugates.
[b]These animals were evaluated on days 10 and 13 at the time of death from radiation sickness.

The cleavable crosslinker confers no therapeutic advantage to anti-CD3-CRM9 immunotoxins and may be less effective (group 3). Cleavable crosslinkers confer some advantage with anti-CD5-CRM9 conjugate in vitro (5) but had no effect in this in vivo system (group 5), and lacked significant potentiating effect when administered with anti-CD3-CRM9 (group 2). The cleavable crosslinker conferred a marked therapeutic advantage to anti-CD5 wild type toxin conjugates and tumor regressions were achieved. However, in these cases the guinea pig toxic dose was exceeded. A single dose on day 7 of cleavable anti-CD5-DT at 6 μg/kg produced 8/10 tumor regressions while a cleavable conjugate made with an irrelevant antibody (OX8) produced no regressions (4/4). However, this dose exceeded the guinea pig MLD by 9 fold. A rescue strategy was tried in which the above conjugate dose was given intravascularly followed by DT antitoxin 4 hours later (also intravascularly). The 4 hr. rescue could not raise the MLD above 0.65 μg/kg. The 1 hr. rescue could not raise the MLD above 0.65 μg/kg. The 1 hr rescue raised the MLD to 36 μg/kg, however, there were no tumor regressions in 10 mice receiving 21.5 μg/kg of the cleavable anti-CD5-DT conjugate.

In groups 7-9 increasing single doses of whole by γ radiation (102 cGy/min) were given to animals bearing 3×3×5 mm tumors. At 400 cGy no complete regressions occurred. At 500 cGy 50% complete tumor regressions occurred. At 600 cGy 100% regression was achieved as judged on day 10 and 13 when the animals died from radiation sickness. (Groups 7-9 did not receive prior radiation and tumor takes were less than 100%).

It appears that the 75 μg/kg anti-CD3-CRM9 (NC) immunotoxin is equal in therapeutic power to between 500 and 600 cGy of radiation.

EXAMPLE 4

Estimation of Cell Kill

The actual cell kill achieved by the radiation and the immunotoxin can be estimated by assuming radiation single hit inactivation kinetics along with a $D_{37}$ value for the radiation. A value for $D_{37}$ of 70-80 cGy with n=1.2-3.0 is not unreasonable for a rapidly dividing helper T cell. $D_{37}$ is the dose of radiation which reduces the fraction of surviving cells to 1/e as extrapolated from the linear portion of the log survivors vs. dose curve and n is the intercept at 0 dose (Anderson and Warner (1976) in Adv. Immunol., Academic Press Inc., 24:257). At a dose of 550 cGy the fraction of surviving cells is calculated to be about $10^{-3}$. Since a majority of tumors completely regress at this dose we estimate that both therapies are producing an approximate 3 log kill. (The remaining cells, $4\times 10^7 \times 10^{-3} = 4\times 10^4$ cells cannot apparently maintain the tumor, i.e., the in vivo plating efficiency is low, a fairly typical situation in the nude mouse xenograft system.) The reliability of this 3 log kill estimate has been verified by determining the tissue culture plating efficiency by limiting dilution of 7 day established Jurkat tumors (following dispersal) and tumors exposed 18 hours earlier in vivo to 600 cGy. Plating efficiencies were 0.14 and $1.4\times 10^{-4}$, respectively. (Plating efficiency is the reciprocal of the minimum average number of cells per well which will grow to form one colony.

It should be emphasized that with high affinity holo-immunotoxins the cell kill is inversely proportional to the target cell number. This presumably occurs because receptors are undersaturated at tolerated doses and free conjugate concentration falls with increasing target cell burden (Marsh and Neville (1987) Ann. N.Y. Acad. Sci. 507:165; Yan et al., submitted) To put this in perspective, the tumor burden in this study is almost equal to the number of T cells in a mouse ($\sim 10^8$). If the extrapolation to humans holds, it could be expected that a tolerated dose of ant-CD3-CRM9 immunotoxin could achieve an in vivo 3 log depletion of a normal number of CD3 positive T cells.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of treating T cell leukemias or lymphomas which carry a CD3 epitope in an animal comprising administering to said animal anti-CD3-CRM9 or derivatives thereof under conditions such that said leukemias or lymphomas regress.

2. A method of treating graft-versus-host disease in an animal by producing at least about a 3 log kill of T cells comprising administering to said animal anti-CD3-CRM9 or derivatives thereof under conditions to produce a 3 log kill of T cells.

3. A non-lethal method of producing at least about a 3 log kill of T cells relative to target cell burden in an animal comprising administering to said animal anti-CD3-CRM9 or derivatives thereof to produce at least about a 3 log kill of T cells relative to target cell burden.

* * * * *